US009170060B2

(12) United States Patent
Beer et al.

(10) Patent No.: US 9,170,060 B2
(45) **Date of Patent: *Oct. 27, 2015**

(54) RAPID MICROFLUIDIC THERMAL CYCLER FOR NUCLEIC ACID AMPLIFICATION

(75) Inventors: Neil Reginald Beer, Pleasanton, CA (US); Kambiz Vafai, Mission Viejo, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 1400 days.

This patent is subject to a terminal disclaimer.

(21) Appl. No.: 12/270,348

(22) Filed: Nov. 13, 2008

(65) Prior Publication Data

US 2009/0226972 A1 Sep. 10, 2009

Related U.S. Application Data

(60) Provisional application No. 61/022,647, filed on Jan. 22, 2008.

(51) Int. Cl.
*C12M 1/00* (2006.01)
*C12M 3/00* (2006.01)
(Continued)

(52) U.S. Cl.
CPC ......... *F28F 13/003* (2013.01); *B01L 3/502784* (2013.01); *B01L 7/52* (2013.01); (Continued)

(58) Field of Classification Search
CPC ... B01L 3/502784; B01L 3/5023; B01L 7/52; B01L 7/00; B01L 2300/0636; B01L 2300/0816; B01L 2300/1838; B01L 2300/185; B01L 2300/0838; B01L 2300/0829; F28F 3/12; F28F 13/003; F28F 2260/02; C12M 41/14; C12M 23/48; C12Q 1/686; C12Q 1/6844; C12Q 1/689; C12Q 1/6853; C12Q 1/6848; C12Q 1/6827; C12Q 1/6816; C12Q 1/6869; C12Q 600/156
USPC ......................................... 435/6, 91.2, 303.1
See application file for complete search history.

(56) References Cited

U.S. PATENT DOCUMENTS

| | | | |
|---|---|---|---|
| 4,683,195 | A | 7/1987 | Mullis |
| 4,683,202 | A | 7/1987 | Mullis |

(Continued)

OTHER PUBLICATIONS

International Preliminary Report on Patentability for WO 2009/094061 A1 (Jun. 2, 2009).*

(Continued)

*Primary Examiner* — Michael Hobbs
(74) *Attorney, Agent, or Firm* — Fenwick & West, LLP

(57) ABSTRACT

A system for thermal cycling a material to be thermal cycled including a microfluidic heat exchanger; a porous medium in the microfluidic heat exchanger; a microfluidic thermal cycling chamber containing the material to be thermal cycled, the microfluidic thermal cycling chamber operatively connected to the microfluidic heat exchanger; a working fluid at first temperature; a first system for transmitting the working fluid at first temperature to the microfluidic heat exchanger; a working fluid at a second temperature, a second system for transmitting the working fluid at second temperature to the microfluidic heat exchanger; a pump for flowing the working fluid at the first temperature from the first system to the microfluidic heat exchanger and through the porous medium; and flowing the working fluid at the second temperature from the second system to the heat exchanger and through the porous medium.

17 Claims, 7 Drawing Sheets

(51) Int. Cl.

*F28F 13/00* (2006.01)
*B01L 7/00* (2006.01)
*F28F 3/12* (2006.01)
*B01L 3/00* (2006.01)

(52) U.S. Cl.

CPC ................ *F28F 3/12* (2013.01); *B01L 3/5023* (2013.01); *B01L 2300/0636* (2013.01); *B01L 2300/0816* (2013.01); *B01L 2300/0838* (2013.01); *B01L 2300/185* (2013.01); *B01L 2300/1838* (2013.01); *F28F 2260/02* (2013.01)

(56) References Cited

U.S. PATENT DOCUMENTS

| | | | |
|---|---|---|---|
| 5,834,252 A | 11/1998 | Stemmer et al. |
| 2002/0119535 A1 | 8/2002 | Slater et al. |
| 2003/0165946 A1 | 9/2003 | Evans |
| 2004/0086927 A1 | 5/2004 | Atwood et al. |
| 2005/0221373 A1 | 10/2005 | Enzelberger et al. |
| 2005/0252773 A1 | 11/2005 | McBride et al. |
| 2005/0282224 A1 | 12/2005 | Fouillet et al. |
| 2006/0042785 A1 | 3/2006 | Werner et al. |
| 2006/0094108 A1 | 5/2006 | Yoder et al. |
| 2008/0166793 A1 | 7/2008 | Beer et al. |
| 2009/0226971 A1 | 9/2009 | Beer et al. |

OTHER PUBLICATIONS

Written Opinion of the International Searching Authority for WO 2009/094061 A1 (Jul. 27, 2010).*

K. Khanafer, K. Vafai: "Isothermal surface production and regulation for high heat flux applications utilizing porous inserts", International Journal of Heat and Mass Transfer vol. 44, 2001, pp. 2933-2947, XP002528304 col. 2, line 5-col. 3, line 14.

Shadi Mahjoob, et al, "Rapid microfluidic thermal cycler for polymerase chain reaction nucleic acid amplification", Intern'l Journal of Heat and Mass Transfer 51(2008) 2109-2122.

N. Reginald Beer, et al "On-Chip Single-Copy Real-Time Reverse-Transcription PCR in Isolated Picoliter Droplets",Analytical Chemistry, vol. 80, No. 6, Mar. 15, 2008, 1854-1858.

PCT International Search Report, PCT Application No. PCT/US2008/083728, Jun. 2, 2009, three pages.

Sambrook, J. et al., "Molecular Cloning: A Laboratory Manual, Chapter 10.47," 2001, vol. 2, Third Edition, Cold Spring Harbor Laboratory Press, New York, USA.

* cited by examiner

RAPID MICROFLUIDIC THERMAL CYCLER FOR NUCLEIC ACID AMPLIFICATION

CROSS-REFERENCE TO RELATED APPLICATIONS

The present application claims benefit under 35 U.S.C. §119(e) of U.S. Provisional Patent Application No. 61/022,647 filed on Jan. 22, 2008 entitled "rapid microfluidic thermal cycler for nucleic acid amplification," the disclosure of which is hereby incorporated by reference in its entirety for all purposes. Related inventions are disclosed and claimed in U.S. patent application Ser. No. 12/270,030 titled Portable Rapid Microfluidic Thermal Cycler for Extremely Fast Nucleic Acid Amplification filed on Nov. 13, 2008. The disclosure of U.S. patent application Ser. No. 12/270,030 titled Portable Rapid Microfluidic Thermal Cycler for Extremely Fast Nucleic Acid Amplification is hereby incorporated by reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND OF THE INVENTION

1. Field of Endeavor

The present invention relates to thermal cycling and more particularly to a rapid microfluidic thermal cycler.

2. State of Technology

U.S. Pat. No. 7,133,726 for a thermal cycler for PCR states: "Generally, in the case of PCR, it is desirable to change the sample temperature between the required temperatures in the cycle as quickly as possible for several reasons. First the chemical reaction has an optimum temperature for each of its stages and as such less time spent at non-optimum temperatures means a better chemical result is achieved. Secondly a minimum time is usually required at any given set point which sets minimum cycle time for each protocol and any time spent in transition between set points adds to this minimum time. Since the number of cycles is usually quite large, this transition time can significantly add to the total time needed to complete the amplification." U.S. Pat. No. 7,133,726 includes the additional state of technology information below:

> "To amplify DNA (Deoxyribose Nucleic Acid) using the PCR process, it is necessary to cycle a specially constituted liquid reaction mixture through several different temperature incubation periods. The reaction mixture is comprised of various components including the DNA to be amplified and at least two primers sufficiently complementary to the sample DNA to be able to create extension products of the DNA being amplified. A key to PCR is the concept of thermal cycling: alternating steps of melting DNA, annealing short primers to the resulting single strands, and extending those primers to make new copies of double-stranded DNA. In thermal cycling the PCR reaction mixture is repeatedly cycled from high temperatures of around 90° C. for melting the DNA, to lower temperatures of approximately 40° C. to 70° C. for primer annealing and extension. Generally, it is desirable to change the sample temperature to the next temperature in the cycle as rapidly as possible. The chemical reaction has an optimum temperature for each of its stages. Thus, less time spent at non optimum temperature means a better chemical result is achieved. Also a minimum time for holding the reaction mixture at each incubation temperature is required after each said incubation temperature is reached. These minimum incubation times establish the minimum time it takes to complete a cycle. Any time in transition between sample incubation temperatures is time added to this minimum cycle time. Since the number of cycles is fairly large, this additional time unnecessarily heightens the total time needed to complete the amplification.
>
> In some previous automated PCR instruments, sample tubes are inserted into sample wells on a metal block. To perform the PCR process, the temperature of the metal block is cycled according to prescribed temperatures and times specified by the user in a PCR protocol file. The cycling is controlled by a computer and associated electronics. As the metal block changes temperature, the samples in the various tubes experience similar changes in temperature. However, in these previous instruments differences in sample temperature are generated by non-uniformity of temperature from place to place within the sample metal block. Temperature gradients exist within the material of the block, causing some samples to have different temperatures than others at particular times in the cycle. Further, there are delays in transferring heat from the sample block to the sample, and those delays differ across the sample block. These differences in temperature and delays in heat transfer cause the yield of the PCR process to differ from sample vial to sample vial. To perform the PCR process successfully and efficiently and to enable so-called quantitative PCR, these time delays and temperature errors must be minimized to the greatest extent possible. The problems of minimizing non-uniformity in temperature at various points on the sample block, and time required for and delays in heat transfer to and from the sample become particularly acute when the size of the region containing samples becomes large as in the standard 8 by 12 microtiter plate.
>
> Another problem with current automated PCR instruments is accurately predicting the actual temperature of the reaction mixture during temperature cycling. Because the chemical reaction or the mixture has an optimum temperature for each of its stages, achieving that actual temperature is critical for good analytical results. Actual measurement of the temperature of the mixture in each vial is impractical because of the small volume of each vial and the large number of vials."

United States Published Patent No. 2005/0252773 for a thermal reaction device and method for using the same includes the following state of technology information:

> "Devices with the ability to conduct nucleic acid amplifications would have diverse utilities. For example, such devices could be used as an analytical tool to determine whether a particular target nucleic acid of interest is present or absent in a sample. Thus, the devices could be utilized to test for the presence of particular pathogens (e.g., viruses, bacteria or fungi), and for identification purposes (e.g., paternity and forensic applications). Such devices could also be utilized to detect or characterize specific nucleic acids previously correlated with particular diseases or genetic disorders. When used as analytical tools, the devices could also be utilized to conduct genotyping analyses and gene expression analyses (e.g., differential gene expression studies).

Alternatively, the devices can be used in a preparative fashion to amplify sufficient nucleic acid for further analysis such as sequencing of amplified product, cell-typing, DNA fingerprinting and the like. Amplified products can also be used in various genetic engineering applications, such as insertion into a vector that can then be used to transform cells for the production of a desired protein product."

United States Published Patent No. 2008/0166793 by Neil Reginald Beer for sorting, amplification, detection, and identification of nucleic acid subsequences in a complex mixture provides the following state of technology information:

"A complex environmental or clinical sample 201 is prepared using known physical (ultracentrifugation, filtering, diffusion separation, electrophoresis, cytometry etc.), chemical (pH), and biological (selective enzymatic degradation) techniques to extract and separate target nucleic acids or intact individual particles 205 (e.g., virus particles) from background (i.e., intra- and extracellular RNA/DNA from host cells, pollen, dust, etc.). This sample, containing relatively purified nucleic acid or particles containing nucleic acids (e.g., viruses), can be split into multiple parallel channels and mixed with appropriate reagents required for reverse transcription and subsequent PCR (primers/probes/dNTPs/enzymes/buffer). Each of these mixes are then introduced into the system in such a way that statistically no more than a single RNA/DNA is present in any given microreactor. For example, a sample containing 106 target RNA/DNA would require millions of microreactors to ensure single RNA/DNA distribution.

An amplifier 207 provides Nucleic Acid Amplification. This may be accomplished by the Polymerase Chain Reaction (PCR) process, an exponential process whereby the amount of target DNA is doubled through each reaction cycle utilizing a polymerase enzyme, excess nucleic acid bases, primers, catalysts (MgCl2), etc. The reaction is powered by cycling the temperature from an annealing temperature whereby the primers bind to single-stranded DNA (ssDNA) through an extension temperature whereby the polymerase extends from the primer, adding nucleic acid bases until the complement strand is complete, to the melt temperature whereby the newly-created double-stranded DNA (dsDNA) is denatured into 2 separate strands. Returning the reaction mixture to the annealing temperature causes the primers to attach to the exposed strands, and the next cycle begins.

The heat addition and subtraction powering the PCR chemistry on the amplifier device 207 is described by the relation:

$$Q=hA(T_{wall}-T_{\infty})$$

The amplifier 207 amplifies the organisms 206. The nucleic acids 208 have been released from the organisms 206 and the nucleic acids 208 are amplified using the amplifier 207. For example, the amplifier 207 can be a thermocycler. The nucleic acids 208 can be amplified in-line before arraying them. As amplification occurs, detection of fluorescence-labeled TaqMan type probes occurs if desired. Following amplification, the system does not need decontamination due to the isolation of the chemical reactants."

U.S. Pat. No. 3,635,037 for a Peltier-effect heat pump provides the following state of technology information:

"The Peltier-effect has been used heretofore in heat pumps for the heating or cooling of areas and substances in which fluid-refrigeration cycles are disadvantageous. For example, for small lightweight refrigerators, compressors, evaporators and associated components of a vapor/liquid refrigerating cycle may be inconvenient and it has, therefore, been proposed to use the heat pump action of a Peltier pile. The Peltier effect may be described as a thermoelectric phenomenon whereby heat is generated or abstracted at the junction of dissimilar metals or other conductors upon application of an electric current. For the most part, a large number of junctions is required for a pronounced thermal effect and, consequently, the Peltier junctions form a pile or battery to which a source of electrical energy may be connected. The Peltier conductors and their junctions may lie in parallel or in series-parallel configurations and may have substantially any shape. For example, a Peltier battery or pile may be elongated or may form a planar or three-dimensional (cubic or cylindrical) array. When the Peltier effect is used in a heat pump, the Peltier battery or pile is associated with a heat sink or heat exchange jacket to which heat transfer is promoted, the heat exchanger being provided with ribs, channels or the like to facilitate heat transfer to or from the Peltier pile over a large surface area of high thermal conductivity. A jacket of aluminum or other metal of high thermal conductivity may serve for this purpose."

International Patent Application No. WO2008070198 by California Institute of Technology published Jun. 12, 2008 entitled "thermal cycling system" provides the following state of technology information:

"Invented in 1983 by Kary Mullis, PCR is recognized as one of the most important scientific developments of the twentieth century. PCR has revolutionized molecular biology through vastly extending the capability to identify and reproduce genetic materials such as DNA. Nowadays PCR is routinely practiced in medical and biological research laboratories for a variety of tasks, such as the detection of hereditary diseases, the identification of genetic fingerprints, the diagnosis of infectious diseases, the cloning of genes, paternity testing, and DNA computing. The method has been automated through the use of thermal stable DNA polymerases and a machine commonly referred to as "thermal cycler."

The conventional thermal cycler has several intrinsic limitations. Typically a conventional thermal cycler contains a metal heating block to carry out the thermal cycling of reaction samples. Because the instrument has a large thermal mass and the sample vessels have low heat conductivity, cycling the required levels of temperature is inefficient. The ramp time of the conventional thermal cycler is generally not rapid enough and inevitably results in undesired non-specific amplification of the target sequences. The suboptimal performance of a conventional thermal cycler is also due to the lack of thermal uniformity widely acknowledged in the art. Furthermore, the conventional real-time thermal cycler system carries optical detection components that are bulky and expensive. Mitsuhashi et al. (U.S. Pat. No. 6,533,255) discloses a liquid metal PCR thermal cycler.

There thus remains a considerable need for an alternative thermal cycler design. A desirable device would allow (a) rapid and uniform transfer of heat to effect a more specific amplification reaction of nucleic acids; and/or (b) real-time monitoring of the progress of the amplification reaction in real time. The present invention satisfies these needs and provides related advantages as well.

In one embodiment, a thermal cycler body (101; 151) comprises a fan (103; 153) and a removable heat block assembly, or swap block (105; 155) (FIG. 1). The swap block (105; 155) is inserted into and removed from the thermal cycler body (103; 153) by optionally sliding the swap heat block on sliding rails (113;163). After the swap block (105; 155) is inserted into the thermal cycler body (103; 153) the door of the thermal cycler (115;165) may be closed. The swap heat block (105; 155) comprises a liquid composition container (111; 161) and a heat sink (107;157) and optionally capped samples (109; 159). In one embodiment the swap heat block (FIG. 2) comprises a receptacle with wells that seals the in the liquid composition so that the sample vessels do not contact the liquid (metal, metal alloy or metal slurry). In another embodiment the swap block (105; 155) comprises a receptacle barrier with wells (307;407) that is sealed to a liquid composition container housing (311; 411), wherein the seal is liquid tight and may optionally comprise a gasket (309;409), (FIGS. 3 and 4). Further, the liquid composition container housing (311;411) is sealed to a base plate (313;413), which may be a metal plate (such as copper or aluminum), wherein the seal is liquid tight and may optionally comprise a gasket (312; 412). The base plate (313;413) is in turn thermally coupled to a Peltier element (315;415), heats and cools the liquid composition and is in turn coupled to a heat sink (417). Optionally, a heat spreader (such as a copper, aluminum, or other metal or metal alloy that has high thermal conductivity) is sandwiched between the base plate (313;413) and the Peltier element (315;415). In some embodiments the swap block (105; 155) is held together by fasteners, such as screws (301;401). In one embodiment the swap block comprises a first piece, such as a receptacle with 48 wells (307;407), that is occupied by a second piece, such as a sample vessel, including but not limited to a sample plate (305;405), a single sample vessel or a strip of sample vessels, into which a third piece, such as a transparent cap plate (303;403), a single cap or strip of caps is inserted In one embodiment the a transparent cap plate (303;403), a single cap or strip of caps optionally comprises an extrusion, such as a light guide."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

In one embodiment the present invention provides an apparatus for thermal cycling a material to be thermal cycled including a microfluidic heat exchanger; a porous medium in the microfluidic heat exchanger; a microfluidic thermal cycling chamber containing the material to be thermal cycled, the microfluidic thermal cycling chamber operatively connected to the microfluidic heat exchanger; a working fluid at first temperature; a first system for transmitting the working fluid at first temperature to the microfluidic heat exchanger; a working fluid at a second temperature, a second system for transmitting the working fluid at second temperature to the microfluidic heat exchanger; a pump for flowing the working fluid at the first temperature from the first system to the microfluidic heat exchanger and through the porous medium; and flowing the working fluid at the second temperature from the second system to the heat exchanger and through the porous medium.

In one embodiment the first system for transmitting the working fluid at first temperature to the microfluidic heat exchanger is a first container for containing the working fluid at first temperature and the second system for transmitting the working fluid at second temperature to the microfluidic heat exchanger is a second container for containing the working fluid at second temperature. In another embodiment the first system for transmitting the working fluid at first temperature to the microfluidic heat exchanger and the second system for transmitting the working fluid at second temperature to the microfluidic heat exchanger comprises a single container and separate line with a heater or cooler that are connected to provide the working fluid at first temperature to the microfluidic heat exchanger and to provide the working fluid at second temperature to the microfluidic heat exchanger.

In one embodiment the present invention provides an apparatus for thermal cycling a material to be thermal cycled. The apparatus includes a microfluidic heat exchanger; a porous medium in the microfluidic heat exchanger; a microfluidic thermal cycling chamber containing the material to be thermal cycled, the microfluidic thermal cycling chamber operatively connected to the microfluidic heat exchanger; a working fluid at first temperature, a first container for containing the working fluid at first temperature, a working fluid at a second temperature, a second container for containing the working fluid at second temperature, a pump for flowing the working fluid at the first temperature from the first container to the microfluidic heat exchanger and through the porous medium; and flowing the working fluid at the second temperature from the second container to the heat exchanger and through the porous medium. In one embodiment the porous medium is a porous medium with uniform porosity. In another embodiment the porous medium is a porous medium with uniform permeability. In another embodiment the apparatus for thermal cycling includes a working fluid at third temperature and a third container for containing the working fluid at third temperature and the pump flows the working fluid at the third temperature from the third container to the microfluidic heat exchanger and through the porous medium.

The present invention also provides a method of thermal cycling a material to be thermal cycled between a number of different temperatures using a microfluidic heat exchanger operatively positioned with respect to the material to be thermal cycled. The method includes the steps of providing working fluid at first temperature, flowing the working fluid at the first temperature to the microfluidic heat exchanger to hold the material to be thermal cycled at the first temperature, providing working fluid at a second temperature, and flowing the working fluid at the second temperature to the heat exchanger to cycle the material to be thermal cycled to the second temperature. The step of flowing the working fluid at the first temperature to the microfluidic heat exchanger and the step of flowing the working fluid at the second temperature to the microfluidic heat exchanger are repeated for a predetermined number of times. One embodiment of the method of thermal cycling includes the step of providing a porous medium in the microfluidic heat exchanger. The step of flowing the working fluid at the first temperature to the microfluidic heat exchanger comprises flowing the working fluid at the first temperature through the porous medium and the step of flowing the working fluid at the second temperature to the microfluidic heat exchanger comprises flowing the working fluid at the second temperature through the porous medium.

The present invention has use in a number of applications. For example, the present invention has use in biowarfare detection applications. The present invention has use in identifying, detecting, and monitoring bio-threat agents that contain nucleic acid signatures, such as spores, bacteria, etc. The present invention has use in biomedical applications. The present invention has use in tracking, identifying, and monitoring outbreaks of infectious disease. The present invention has use in automated processing, amplification, and detection of host or microbial DNA in biological fluids for medical purposes. The present invention has use in genomic analysis, genomic testing, cancer detection, genetic fingerprinting. The present invention has use in forensic applications. The present invention has use in automated processing, amplification, and detection DNA in biological fluids for forensic purposes. The present invention has use in food and beverage safety. The present invention has use in automated food testing for bacterial or viral contamination. The present invention has use in environmental monitoring and remediation monitoring.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
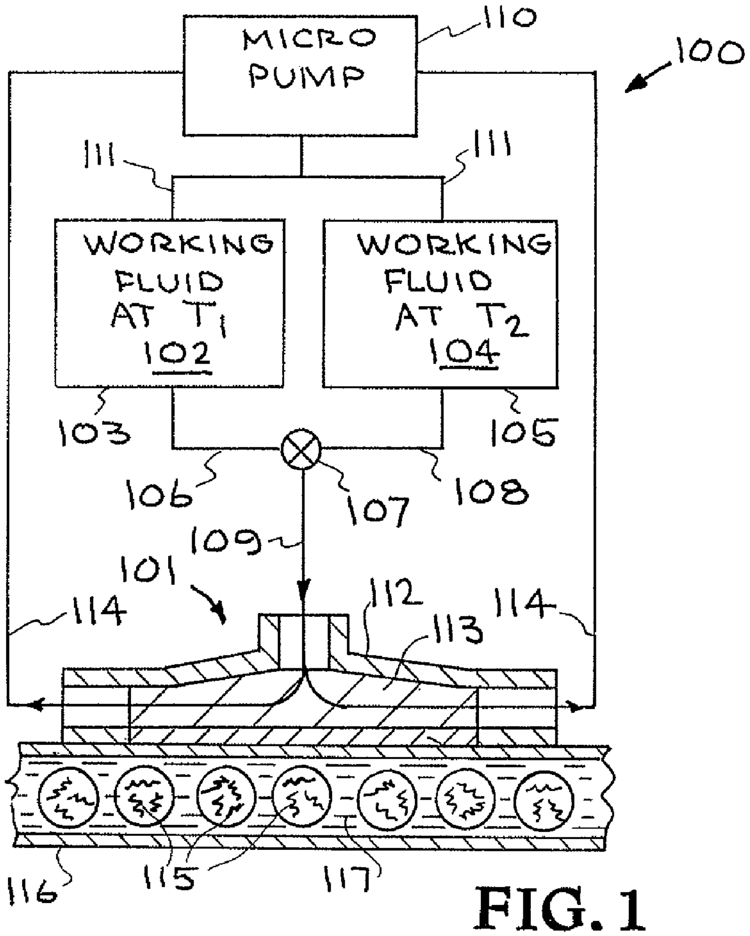
FIG. 1 illustrates one embodiment of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, one embodiment of a thermal cycling system constructed in accordance with the present invention is illustrated. The system is designated generally by the reference numeral 100. The system 100 will be described as a polymerase chain reaction (PCR) system; however, it is to be understood that the system 100 can be used as other thermal cycling systems.

PCR is the gold standard for fast and efficient nucleic acid analysis. It is the best method for genetic analysis, forensics, sequencing, and other critical applications because it is unsurpassed in specificity and sensitivity. By its very nature the method utilizes an exponential increase in signal, allowing detection of even single-copy nucleic acids in complex, real environments. Because of this PCR systems are ubiquitous, and the market for a faster thermocycling method is significant. Recent advancements in microfluidics allow the miniaturization and high throughput of on-chip processes, but they still lack the speed and thermal precision needed to revolutionize the field.

PCR systems can be advanced by microfluidic systems such as reduction of costly reagent volumes, decreased diffusion distances, optical concentration of detection probes, production of massively parallel and inexpensive microfluidic analysis chips, and scalable mass production of such chips. But this also decreases the time to perform each cycle by two orders of magnitude, allowing PCR analysis times to fall from hours (as in the commercially available Cepheid SmartCyclers) to less than one minute with this device, even when operating on long nucleic acids. Additionally, due to utilization of high heat capacity fluids as thermal energy sources, microfluidic systems will enjoy much more accurate and precise thermal control than the existing electrical heating and cooling-based methods such as Peltier devices, resistive trace heaters, resistive tape heaters, etc.

Technologies that could conceivably compete with this art on sample throughput are mainly robotic-based systems, but are far too slow to compete on reaction speed, are far too complex to compete on cost or simplicity, and utilize heating technologies with much less precision and accuracy. These devices typically couple auto-pipettes with robotic manipulators to measure, mix, and deliver sample and reagents. These devices are complex, expensive, and difficult to miniaturize.

Referring again to FIG. 1 the system 100 provides thermal cycling a material 115 to be thermal cycled between a temperature $T_1$ and $T_2$ using a microfluidic heat exchanger 101 operatively positioned with respect to the material 115 to be thermal cycled. A working fluid 102 at $T_1$ is provided and the working fluid 102 at $T_1$ is flowed to the microfluidic heat exchanger 101. A working fluid 104 at $T_2$ is provided and the working fluid 104 at $T_2$ is flowed to the heat exchanger 101. The steps of flowing the working fluid at $T_1$ and at $T_2$ to the microfluidic heat exchanger 101 are repeated for a predetermined number of times. A porous medium 113 is located in the microfluidic heat exchanger 101. The working fluids at $T_1$ and $T_2$ flow through the porous medium 113 during the steps of flowing the working fluid at $T_1$ and $T_2$ through the microfluidic heat exchanger 101.

The steps of repeatedly flowing the working fluid at $T_1$ and at $T_2$ to the microfluidic heat exchanger 101 provide PCR fast and efficient nucleic acid analysis. The microfluidic polymerase chain reaction (PCR) thermal cycling method 100 is capable of extremely fast cycles, and a resulting extremely fast detection time for even long amplicons (amplified nucleic acids). The method 100 allows either singly or in combination: reagent and analyte mixing; cell, virion, or capsid lysing to release the target DNA if necessary; nucleic acid amplification through the polymerase chain reaction (PCR), and nucleic acid detection and characterization through optical or other means. An advantage of this system lies in its complete integration on a microfluidic platform and its extremely fast thermocycling.

The system 100 includes the following structural components: microfluidic heat exchanger 101, microfluidic heat exchanger housing 112, porous medium 113, microfluidic channel 116, fluid 117, micropump 110, lines 111, chamber 103, working fluid 102 at $T_1$, chamber 105, working fluid 104 at $T_2$, lines 108, 3-way valve 107, line 106, line 109, and lines 114.

The structural components of the system 100 having been described, the operation of the system 100 will be explained. The valve 107 is actuated to provide flow of working fluid 102 at $T_1$ from chamber 103 to the microfluidic heat exchanger 101. Micro pump 110 is actuated driving working fluid 102 at $T_1$ from chamber 103 to the microfluidic heat exchanger 101. The working fluid 102 at $T_1$ passes through the porous medium 113 in the microfluidic heat exchanger 101, raising the temperature of the material to be thermal cycled 115 to temperature $T_1$. The porous medium 113 in the microfluidic heat exchanger 101 results in substantial surface area enhancement and increased fluid flow-path tortuosity, both of which enhance heat transfer and the resulting heat flux between the working fluid and the porous matrix.

Next the valve 107 is actuated to provide flow of working fluid 104 at $T_2$ from chamber 105 to the microfluidic heat exchanger 101. Micro pump 110 is actuated driving working fluid 104 at $T_2$ from chamber 105 to the microfluidic heat exchanger 101. The working fluid 102 at $T_2$ passes through the porous medium 113 in the microfluidic heat exchanger 101, lowering the temperature of the material to be thermal cycled 115 to temperature $T_2$. The steps of flowing the working fluid at $T_1$ and at $T_2$ to the microfluidic heat exchanger 101 are repeated for a predetermined number of times to provide the desired PCR. The porous medium 113 in the microfluidic heat exchanger 101 results in substantial surface area enhancement and increased fluid flow-path tortuosity, both of which enhance heat transfer and the resulting heat flux between the working fluid and the porous matrix.

The aqueous channel 117 can be used to mix various assay components (i.e., analyte, oligonucleotides, primer, TaqMan probe, etc.) in preparation for amplification and detection. The channel geometry allows for dividing the sample into multiple aliquots for subsequent analysis serially or in parallel with multiple streams. Samples can be diluted in a continuous stream, partitioned into slugs, or emulsified into droplets. Furthermore, the nucleic acids may be in solution or hybridized to magnetic beads depending on the desired assay. The scalability of the architecture allows for multiple different reactions to be tested against aliquots from the same sample. Decontamination of the channels after a series of runs can easily be performed by flushing the channels with a dilute solution of sodium hypochlorite, followed by deionized water.

The system 100 provides an innovative and comprehensive methodology for rapid thermal cycling utilizing porous inserts 113 for attaining and maintaining a uniform temperature within the PCR microchip unit 100 consisting of all the pertinent layers. This design for PCR accommodates rapid transient and steady cyclic thermal management applications. The system 100 has considerably higher heating/cooling temperature ramps, improved thermal convergence, and lower required power compared to prior art. The result is a very uniform temperature distribution at the substrate at each time step and orders of magnitude faster cycle times than current systems. A comprehensive investigation of the various pertinent heat transfer parameters of the PCR system 100 has been performed.

The heat exchanger 101 of the system 100 utilizes inlet and exit channels where heating/cooling fluid 102 and 104 is passing through an enclosure, and a layer of conductive plate attached to a PCR micro-chip. The enclosure is filled with a conductive porous medium 113 of uniform porosity and permeability. In another embodiment the enclosure is filled with a conductive porous medium 113 with a gradient porosity. The nominal permeability and porosity of the porous matrix are taken as $3.74\times10^{-10}$ $m^2$ and 0.45, respectively. The porous medium 113 is saturated with heating/cooling fluid 102, 104 coming through an inlet channel. The inlet channel will be connected to hot and cold supply tanks 103 and 105. A switching valve 107 is used to switch between hot 103 and cold tanks 105 for heating and cooling cycles. All lateral walls and top of the porous medium are insulated to minimize losses. The micropump 110 is positioned to drive the working fluids 102 and 104 directly into the microfluidic heat exchanger 101. By positioning the micropump 110 outside the hot and cold supply tanks 103 and 105 and lines 106, 108, 109 to the microfluidic heat exchanger 101, and lines 114 from the heat exchanger 101, it eliminates the time that would be required to bring the micropump 110 up to the new temperature after each change.

The material to be thermal cycled 115 is in a PCR chamber 116 connected to the microfluidic heat exchanger 101. An example of a PCR chamber containing the material to be thermal cycled 115 is shown in U.S. Published Patent Application No. 2008/0166793 for sorting, amplification, detection, and identification of nucleic acid subsequences. The disclosure of U.S. Published Patent Application No. 2008/0166793 for sorting, amplification, detection, and identification of nucleic acid subsequences is incorporated herein by reference.

Figure 2:
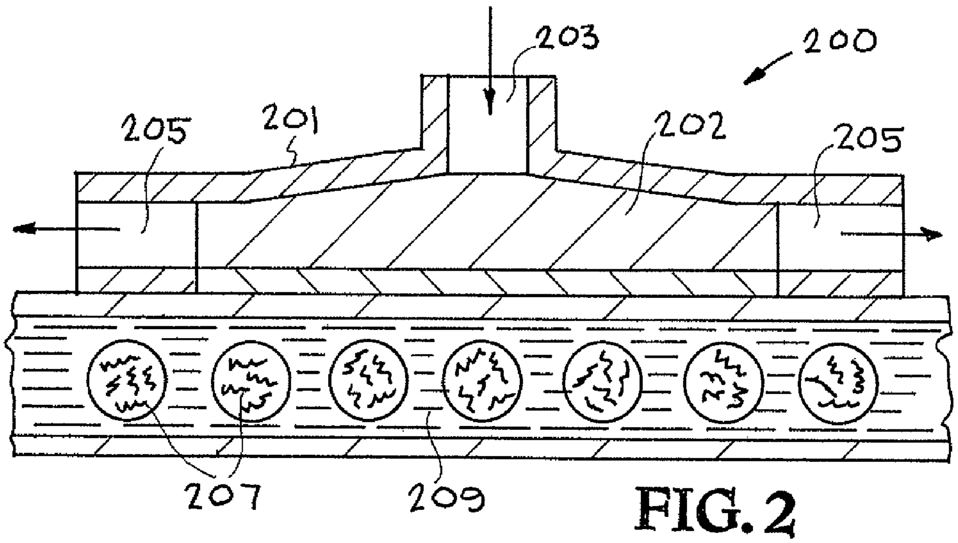
FIG. 2 illustrates another embodiment of the present invention.

Referring now to FIG. 2, another embodiment of a thermal cycling system constructed in accordance with the present invention is illustrated. The system is designated generally by the reference numeral 200. The system 200 provides thermal cycling of a material 207 to be thermal cycled between a temperature $T_1$ and $T_2$ using a microfluidic heat exchanger 201 operatively positioned with respect to the material 207 to be thermal cycled. A working fluid at $T_1$ is provided and the working fluid at $T_1$ is flowed to the microfluidic heat exchanger 201. A working fluid at $T_2$ is provided and the working fluid at $T_2$ is flowed to the heat exchanger 201. The steps of flowing the working fluid at $T_1$ and at $T_2$ to the microfluidic heat exchanger 201 are repeated for a predetermined number of times. A porous medium 202 is located in the microfluidic heat exchanger 201. The working fluids at $T_1$ and $T_2$ flow through the porous medium 202 during the steps of flowing the working fluid at $T_1$ and $T_2$ through the microfluidic heat exchanger 201. The system 200 includes the following structural components: microfluidic heat exchanger 201, porous medium 202, inlet 203, outlet 205, and thermal cycling chamber 209.

The structural components of the system 200 having been described, the operation of the system 200 will be explained. A valve is actuated to provide flow of working fluid at $T_1$ from a chamber to the microfluidic heat exchanger 201. A micro pump is actuated driving working fluid at $T_1$ from chamber to the microfluidic heat exchanger 201. The working fluid at $T_1$ passes through the porous medium 202 in the microfluidic heat exchanger 201 raising the temperature of the material 207 to be thermal cycled to temperature $T_1$. The porous medium 202 in the microfluidic heat exchanger 201 results in substantial surface area enhancement and increased fluid flow-path tortuosity, both of which enhance heat transfer and the resulting heat flux between the working fluid and the porous matrix.

Next a valve is actuated to provide flow of working fluid at $T_2$ from a chamber to the microfluidic heat exchanger 201. A micro pump is actuated driving working fluid at $T_2$ from the chamber to the microfluidic heat exchanger 201. The working fluid at $T_2$ passes through the porous medium 202 in the microfluidic heat exchanger 201 lowering the temperature of the material 207 to be thermal cycled to temperature $T_2$. The steps of flowing the working fluid at $T_1$ and at $T_2$ to the microfluidic heat exchanger 201 are repeated for a predetermined number of times to provide the desired PCR. The porous medium 202 in the microfluidic heat exchanger 201 results in substantial surface area enhancement and increased fluid flow-path tortuosity, both of which enhance heat transfer and the resulting heat flux between the working fluid and the porous matrix.

The aqueous channel can be used to mix various assay components (i.e., analyte, oligonucleotides, primer, TaqMan probe, etc.) in preparation for amplification and detection. The channel geometry allows for dividing the sample into multiple aliquots for subsequent analysis serially or in parallel with multiple streams. Samples can be diluted in a continuous stream, partitioned into slugs, or emulsified into droplets. Furthermore, the nucleic acids may be in solution or hybridized to magnetic beads depending on the desired assay. The scalability of the architecture allows for multiple different reactions to be tested against aliquots from the same sample. Decontamination of the channels after a series of runs can easily be performed by flushing the channels with a dilute solution of sodium hypochlorite, followed by deionized water.

The system 200 provides an innovative and comprehensive methodology for rapid thermal cycling utilizing porous inserts 202 for attaining and maintaining a uniform temperature within the PCR microchip unit 200 consisting of all the pertinent layers. This design for PCR accommodates rapid transient and steady cyclic thermal management applications. The system 200 has considerably higher heating/cooling temperature ramps, better thermal convergence, and lower required power compared to prior art. The result is a very uniform temperature distribution at the substrate at each time step and orders of magnitude faster cycle times than current systems. A comprehensive investigation of the various pertinent heat transfer parameters of the PCR system 200 has been performed.

The heat exchanger 201 of the system 200 utilizes inlet and exit channels where heating/cooling fluid is passing through an enclosure, and a layer of conductive plate attached to a PCR micro-chip or microarray. The enclosure is filled with a conductive porous medium 202 of uniform porosity and permeability. The nominal permeability and porosity of the porous matrix are taken as $3.74\times10^{-10}$ $m^2$ and 0.45, respectively. The porous medium 202 is saturated with heating/cooling fluid coming through an inlet channel. The inlet channel will be connected to hot and cold supply tanks. A switching valve is used to switch between hot and cold tanks for heating and cooling cycles. All lateral walls and top of the porous medium are insulated to minimize losses.

Figure 3:
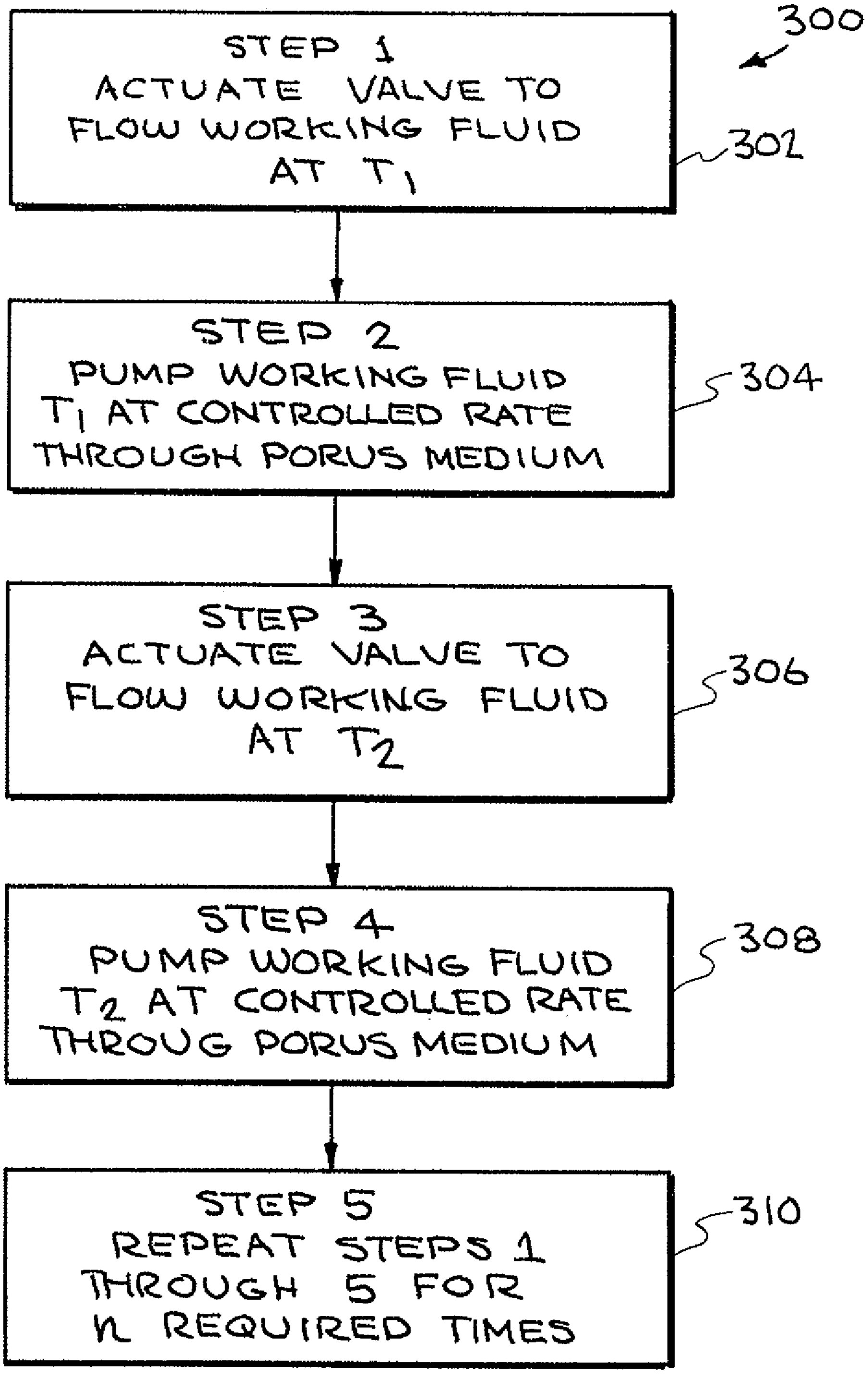
FIG. 3 is a flow chart illustrating one embodiment of the present invention.

Referring now to FIG. 3, a flow chart illustrates another embodiment of a thermal cycling system of the present invention. The system is designated generally by the reference numeral 300. The system 300 provides thermal cycling a material to be thermal cycled between a temperature $T_1$ and $T_2$ using a microfluidic heat exchanger operatively positioned with respect to the material to be thermal cycled.

In step 1 a valve is actuated to flow working fluid at $T_1$. This is designated by the reference numeral 302.

In step 2 a pump is actuated to flow working fluid at $T_1$ at a controlled rate to a microfluidic heat exchanger with a porous medium. This is designated by the reference numeral 304.

In step 3 a valve is actuated to flow working fluid at $T_2$. This is designated by the reference numeral 306.

In step 4 a pump is actuated to flow working fluid at $T_2$ at a controlled rate to a microfluidic heat exchanger with a porous medium. This is designated by the reference numeral 308.

In step 5 the steps 1, 2, 3, and 4 are repeated for the required times. This is designated by the reference numeral 310.

The steps of repeatedly flowing the working fluid at $T_1$ and at $T_2$ to the microfluidic heat exchanger 101 provide PCR fast and efficient nucleic acid analysis. The microfluidic polymerase chain reaction (PCR) thermal cycling method 300 is capable of extremely fast cycles, and a resulting extremely fast detection time for even long amplicons (amplified nucleic acids). The method 300 allows either singly or in combination: reagent and analyte mixing; cell, virion, or capsid lysing to release the target DNA if necessary; nucleic acid amplification through the polymerase chain reaction (PCR), and nucleic acid detection and characterization through optical or other means. An advantage of this system lies in its complete integration on a microfluidic platform and its extremely fast thermocycling.

Alternative Embodiments

Figure 4A:
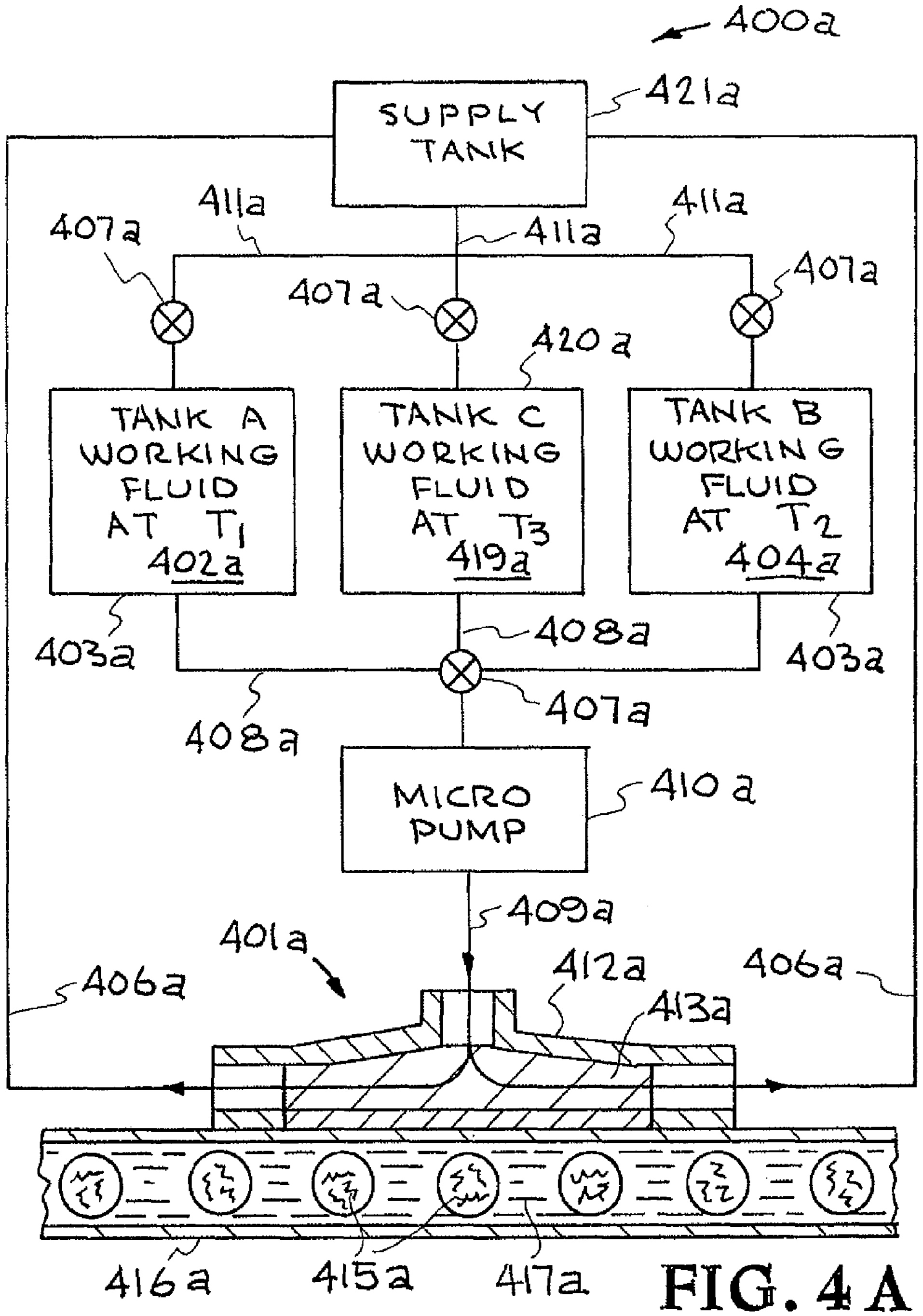
FIGS. 4A and 4B illustrate alternative embodiments of the present invention.

Referring now to FIG. 4A, another embodiment of a thermal cycling system constructed in accordance with the present invention is illustrated. The system is designated generally by the reference numeral 400*a*. The system 400*a* provides thermal cycling of a material 415*a* between different temperatures using a microfluidic heat exchanger 401*a* operatively positioned with respect to the material 415*a*.

A working fluid 402*a* at $T_1$ is provided in "Tank A" 403*a*. The working fluid is maintained at the temperature $T_1$ in Tank A (403*a*) by appropriate heating and cooling equipment. The working fluid 402*a* at $T_1$ from Tank A (403*a*) is flowed to the microfluidic heat exchanger 401*a*.

A working fluid 404*a* at $T_2$ is provided in "Tank B" 405*a*. The working fluid is maintained at the temperature $T_2$ in Tank B (405*a*) by appropriate heating and cooling equipment. The working fluid 404*a* at $T_2$ from Tank B (405*a*) is flowed to the heat exchanger 401*a*.

A working fluid 419*a* at $T_3$ is provided in "Tank C" 420*a*. The working fluid is maintained at the temperature $T_3$ in Tank C (420*a*) by appropriate heating and cooling equipment. The working fluid 419*a* at $T_3$ from Tank C (420*a*) is flowed to the heat exchanger 401*a*. The system 400*a* includes the following additional structural components: microfluidic heat exchanger housing 412*a*, porous medium 413*a*, microfluidic channel 416*a*, fluid 417*a*, micropump 410*a*, lines 411*a*, lines 406*a*, lines 408*a*, multiposition valves 407*a*, line 409*a*, and supply tank 421*a*.

The structural components of the system 400*a* having been described, the operation of the system 400*a* will be explained. The system 400*a* will be described as a polymerase chain reaction (PCR) system; however, it is to be understood that the system 400*a* can be used as other thermal cycling systems. For example the system 400*a* can be used to thermal cycle a multiwall plate or a glass microarray.

When used for PCR, the system 400*a* provides thermal cycling a material 415*a* to be thermal cycled between a temperature $T_1$ and $T_2$ using a microfluidic heat exchanger 401*a* operatively positioned with respect to the material 415*a* to be thermal cycled. A working fluid 402*a* at $T_1$ is provided in "Tank A" 403*a*. The working fluid 402*a* at $T_1$ from Tank A (403*a*) is flowed to the microfluidic heat exchanger 401*a*. A working fluid 404*a* at $T_2$ is provided in "Tank B" 405*a*. The working fluid 404*a* at $T_2$ from Tank B (405*a*) is flowed to the heat exchanger 401*a*. A working fluid 419*a* at $T_3$ is provided in "Tank C" 420*a*. The working fluid 419*a* at $T_3$ from Tank C (420*a*) is flowed to the heat exchanger 401*a*.

The multiposition valves 407*a* are actuated to provide flow of working fluid 402*a* at $T_1$ from Tank A (403*a*) to the microfluidic heat exchanger 401*a*. Micro pump 410*a* is actuated driving working fluid 402*a* at $T_1$ from Tank A (403*a*) to the microfluidic heat exchanger 401*a*. The working fluid 402*a* at $T_1$ passes through the porous medium 413*a* in the microfluidic heat exchanger 401*a* raising the temperature of the material to be thermal cycled 415*a* to temperature $T_1$. The porous medium 413*a* in the microfluidic heat exchanger 401*a* results in substantial surface area enhancement and increased fluid flow-path tortuosity, both of which enhance heat transfer and the resulting heat flux between the working fluid and the porous matrix.

Next the valves 407*a* are actuated to provide flow of working fluid 404*a* at $T_2$ from Tank B (405*a*) to the microfluidic heat exchanger 401*a*. Micro pump 410*a* is actuated driving working fluid 404*a* at $T_2$ from chamber 405*a* to the microfluidic heat exchanger 401*a*. The working fluid 402*a* at $T_2$ passes through the porous medium 413*a* in the microfluidic heat exchanger 401*a* lowering the temperature of the material to be thermal cycled 415*a* to temperature $T_2$. The porous medium 413 in the microfluidic heat exchanger 401*a* results in substantial surface area enhancement and increased fluid flow-path tortuosity, both of which enhance heat transfer and the resulting heat flux between the working fluid and the porous matrix.

The valves 407*a* can also be actuated to provide flow of working fluid 419*a* at $T_3$ from Tank C (420*a*) to the microfluidic heat exchanger 401*a*. Micro pump 410*a* is actuated driving working fluid 419*a* at $T_3$ from Tank C (420*a*) to the microfluidic heat exchanger 401*a*. The working fluid 402*a* at $T_3$ passes through the porous medium 413*a* in the microfluidic heat exchanger 401*a* changing the temperature of the material to be thermal cycled 415*a* to temperature $T_3$. The porous medium 413 in the microfluidic heat exchanger 401*a*

In performing PCR of Nucleic acids, the system 400*a* can be used to mix various assay components (i.e., analyte, oligonucleotides, primer, TaqMan probe, etc.) in preparation for amplification and detection. The steps of flowing the working fluid at $T_1$ and at $T_2$ to the microfluidic heat exchanger 401*a* can be repeated for a predetermined number of times to provide the desired PCR. The channel geometry allows for dividing the sample into multiple aliquots for subsequent analysis serially or in parallel with multiple streams. Samples can be diluted in a continuous stream, partitioned into slugs, or emulsified into droplets. Furthermore, the nucleic acids may be in solution or hybridized to magnetic beads depending on the desired assay. The scalability of the architecture allows for multiple different reactions to be tested against aliquots from the same sample. Decontamination of the channels after a series of runs can easily be performed by flushing the channels with a dilute solution of sodium hypochlorite, followed by deionized water.

The system 401*a* can also be used for other thermal cycling than PCR. The heat exchanger 401*a* of the system 400*a* utilizes inlet and exit channels where heating/cooling fluid 402*a*, 404*a*, and 419*a* pass through the porous media 413*a*. In one embodiment the porous media 413*a* has a uniform porosity and permeability. The nominal permeability and porosity of the porous matrix are taken as $3.74\times10^{-10}$ $m^2$ and 0.45, respectively. In other embodiments the porous media 413*a* has gradient porosity. The system 400*a* allows the heat exchanger 401*a* to change the temperature of the material to be thermal cycled 415 between and to a variety of different temperatures. By various combinations of settings of the multiposition valves 407*a* it is possible to supply working fluid from tanks A, B, and C at a near infinite variety of different temperatures. This provides a full spectrum of heat transfer control by a combination of $T_1$, $T_2$, and $T_3$ as well as coolant flow rate.

The thermal engine of the present invention can be used for other thermal cycling than PCR. For example, embodiments of the present invention will work with all of the following geometries/applications: (a) Closed and open microchannels; (b) Open geometries (microdroplets on a planar substrate—see "Chip-based device for coplanar sorting, amplification, detection, and identification of nucleic acid subsequences in a complex mixture as illustrated by U.S. Published Patent Application No. 2008/0166793 for sorting, amplification, detection, and identification of nucleic acid subsequences; (c) microarrays, such as the Affymetrix GeneChip, NimbleGen, and others (PCR can be performed on the microarray if the array has primers bound to the surface); (d) PCR well plates (96 well, 384 well, 1536 etc.); and (e) Individual cuvettes (For example, the Cepheid SmartCycler). The method/apparatus of the present invention does not have to be PCR only. It can be thermal cycling for: (a) PCR with real-time optical detection, (b) PCR with real-time non-optical detection (electrical charge), (c) PCR with endpoint detection (not real time), (d) PCR with pyrosequencing, 4-color sequencing, or other sequencing at the end, (e) sequencing only (no PCR), and (f) Chemical synthesis (including crystallography).

Figure 4B:
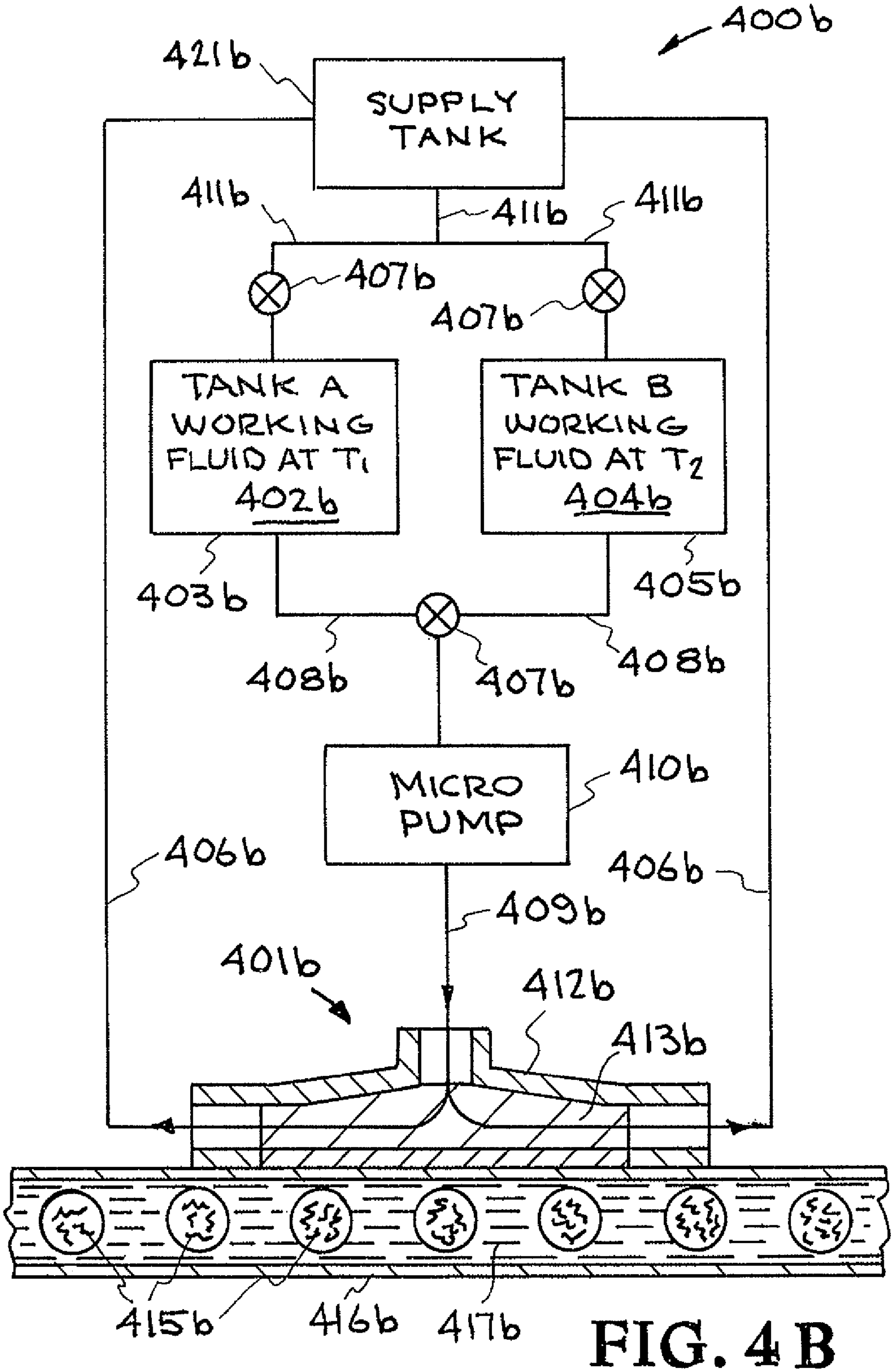

Referring now to FIG. 4B, another embodiment of a thermal cycling system constructed in accordance with the present invention is illustrated. The system is designated generally by the reference numeral 400*b*. The system 400*b* provides thermal cycling of a material 415*b* between different temperatures using a microfluidic heat exchanger 401*b* operatively positioned with respect to the material 415*b*.

A working fluid 402*b* at $T_1$ is provided in "Tank A" 403*b*. The working fluid is maintained at the temperature $T_1$ in Tank A (403*b*) by appropriate heating and cooling equipment. The working fluid 402*b* at $T_1$ from Tank A (403*b*) is flowed to the microfluidic heat exchanger 401*b*.

A working fluid 404*b* at $T_2$ is provided in "Tank B" 405*b*. The working fluid is maintained at the temperature $T_2$ in Tank B (405*b*) by appropriate heating and cooling equipment. The working fluid 404*b* at $T_2$ from Tank B (405*b*) is flowed to the heat exchanger 401*b*.

The system 400*b* includes the following additional structural components: microfluidic heat exchanger housing 412*b*, porous medium 413*b*, microfluidic channel 416*b*, fluid 417*b*, micropump 410*b*, lines 411*b*, lines 406*b*, lines 408*b*, multiposition valves 407*b*, line 409*b*, and supply tank 421*b*.

The structural components of the system 400*b* having been described, the operation of the system 400*b* will be explained. The system 400*b* will be described as a polymerase chain reaction (PCR) system; however, it is to be understood that the system 400*b* can be used as other thermal cycling systems. For example the system 400*b* can be used to thermal cycle a multiwall plate or a glass microarray.

When used for PCR, the system 400*b* provides thermal cycling a material 415*b* to be thermal cycled between a temperature $T_1$ and $T_2$ using a microfluidic heat exchanger 401*b* operatively positioned with respect to the material 415*b* to be thermal cycled. A working fluid 402*b* at $T_1$ is provided in "Tank A" 403*b*. The working fluid 402*b* at $T_1$ from Tank A 403*b* is flowed to the microfluidic heat exchanger 401*b*. A working fluid 404*b* at $T_2$ is provided in "Tank B" 405*b*. The working fluid 404*b* at $T_2$ from Tank B 405*b* is flowed to the heat exchanger 401*b*.

The multiposition valves 407*b* are actuated to provide flow of working fluid 402*b* at $T_1$ from Tank A (403*b*) to the microfluidic heat exchanger 401*b*. Micro pump 410*b* is actuated driving working fluid 402*b* at $T_1$ from Tank A (403*b*) to the microfluidic heat exchanger 401*b*. The working fluid 402*b* at $T_1$ passes through the porous medium 413*b* in the microfluidic heat exchanger 401*b* raising the temperature of the material to be thermal cycled 415*b* to temperature $T_1$. The porous medium 413*b* in the microfluidic heat exchanger 401*b* results in substantial surface area enhancement and increased fluid flow-path tortuosity, both of which enhance heat transfer and the resulting heat flux between the working fluid and the porous matrix.

Next the valve 407*b* is actuated to provide flow of working fluid 404*b* at $T_2$ from Tank B (405*b*) to the microfluidic heat exchanger 401*b*. Micro pump 410*b* is actuated driving working fluid 404*b* at $T_2$ from Tank B (405*b*) to the microfluidic heat exchanger 401*b*. The working fluid 402*b* at $T_2$ passes through the porous medium 413*b* in the microfluidic heat exchanger 401*b* lowering the temperature of the material to be thermal cycled 415*b* to temperature $T_2$. The porous medium 413 in the microfluidic heat exchanger 401*b* results in substantial surface area enhancement and increased fluid flow-path tortuosity, both of which enhance heat transfer and the resulting heat flux between the working fluid and the porous matrix.

In performing PCR of Nucleic acids, the system 400*b* can be used to mix various assay components (i.e., analyte, oligonucleotides, primer, TaqMan probe, etc.) in preparation for amplification and detection. The steps of flowing the working fluid at $T_1$ and at $T_2$ to the microfluidic heat exchanger 401*b* can be repeated for a predetermined number of times to provide the desired PCR. The channel geometry allows for dividing the sample into multiple aliquots for subsequent analysis serially or in parallel with multiple streams. Samples can be diluted in a continuous stream, partitioned into slugs, or emulsified into droplets. Furthermore, the nucleic acids may be in solution or hybridized to magnetic beads depending on the desired assay. The scalability of the architecture allows for multiple different reactions to be tested against aliquots from the same sample. Decontamination of the channels after a series of runs can easily be performed by flushing the channels with a dilute solution of sodium hypochlorite, followed by deionized water.

The system 401*b* can also be used for thermal cycling other than PCR. The heat exchanger 401*b* of the system 400*b* utilizes inlet and exit channels where heating/cooling fluid 402*b* and 404*b* pass through the porous media 413*b*. In one embodiment the porous media 413*b* has a uniform porosity and permeability. The nominal permeability and porosity of the porous matrix are taken as $3.74\times10^{-10}$ $m^2$ and 0.45, respectively. In other embodiments the porous media 413*b* has gradient porosity. The system 400*b* allows the heat exchanger 401*b* to change the temperature of the material to be thermal cycled 415 between and to a variety of different temperatures. By various combinations of settings of the multiposition valve 407*b* it is possible to supply working fluid from tanks A and B at a near infinite variety of different temperatures. This provides a full spectrum of heat transfer control by a combination of $T_1$ & $T_2$, as well as coolant flow rate.

Multiwell Plate

Figure 5:
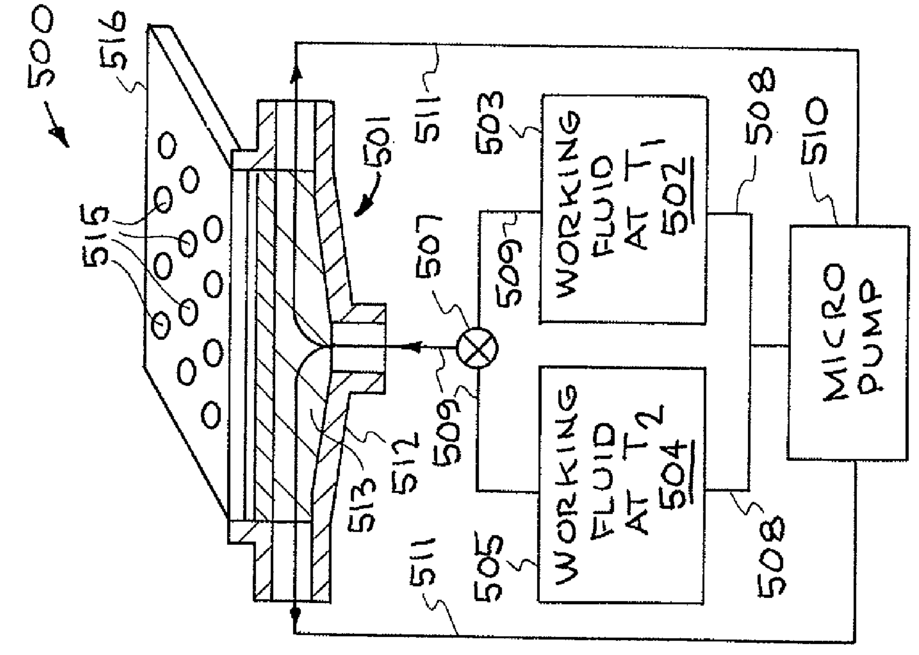
FIG. 5 illustrates an embodiment of the present invention wherein the material to be thermalcycled is in a multiwell plate.

Referring now to FIG. 5, another embodiment of a thermal cycling system constructed in accordance with the present invention is illustrated. The system is designated generally by the reference numeral 500. The system 500 provides thermal cycling a material 515 to be thermal cycled between different temperatures using a microfluidic heat exchanger 501 operatively positioned with respect to the material 515 to be thermal cycled. The material 515 to be thermal cycled is contained within a multiwell plate 116. Examples of multiwall plates are shown in U.S. Pat. No. 7,410,618 for a multiwell plate which states, "Multiwell plates are known in the prior art which are commonly used for bioassays. Each multiwell plate includes a multiwell plate body having an array of wells formed therein, typically having 96, 384, or 1,536 wells." U.S. Pat. No. 7,410,618 for a multiwell plate is incorporated herein by reference.

The system 500 includes the following additional structural components: microfluidic heat exchanger housing 512, porous medium 513, micropump 510, lines 511, chamber 503, working fluid 502 at $T_1$, chamber 505, working fluid 504 at $T_2$, lines 508, multi-position valve 507, and lines 509.

The structural components of the system 500 having been described, the operation of the system 500 will be explained. The multi-position valve 507 is actuated to provide flow of working fluid 502 at $T_1$ from chamber 503 to the microfluidic heat exchanger 501. Micro pump 510 is actuated driving working fluid 502 at $T_1$ from chamber 503 to the microfluidic heat exchanger 501. The working fluid 502 at $T_1$ passes through the porous medium 513 in the microfluidic heat exchanger 501 raising the temperature of the material to be thermal cycled 515 to temperature $T_1$. The porous medium 513 in the microfluidic heat exchanger 501 results in substantial surface area enhancement and increased fluid flow-path tortuosity, both of which enhance heat transfer and the resulting heat flux between the working fluid and the porous matrix.

Next the multi-position valve 507 is actuated to provide flow of working fluid 504 at $T_2$ from chamber 505 to the microfluidic heat exchanger 501. Micro pump 510 is actuated driving working fluid 504 at $T_2$ from chamber 505 to the microfluidic heat exchanger 501. The working fluid 502 at $T_2$ passes through the porous medium 513 in the microfluidic heat exchanger 501 lowering the temperature of the material to be thermal cycled 515 to temperature $T_2$.

The heat exchanger 501 of the system 500 utilizes inlet and exit channels where heating/cooling fluid 502 and 504 is passing through an enclosure, and a layer of multiwell plate 516 containing the material to be thermal cycled. The heat exchange 501 is filled with a conductive porous medium 513 of uniform porosity and permeability. In another embodiment the enclosure is filled with a conductive porous medium 513 with a gradient porosity. The nominal permeability and porosity of the porous matrix are taken as $3.74\times10^{-10}$ $m^2$ and 0.45, respectively. The porous medium 513 is saturated with heating/cooling fluid 502, 504 coming through an inlet channel. The inlet channel will be connected to hot and cold supply tanks 503 and 505. The switching multi-position valve 507 is used to switch between hot 502 and cold tanks 505 for heating and cooling cycles. All lateral walls and top of the porous medium are insulated to minimize losses. The micropump 510 is positioned to drive the working fluids 502 and 504 directly into the microfluidic heat exchanger 501. By positioning the micropump 510 outside the hot and cold supply tanks 503 and 505 and lines to the microfluidic heat exchanger 501 it eliminates the time that would be required to bring the micropump 510 up to the new temperature after each change.

Microarray

Figure 6:
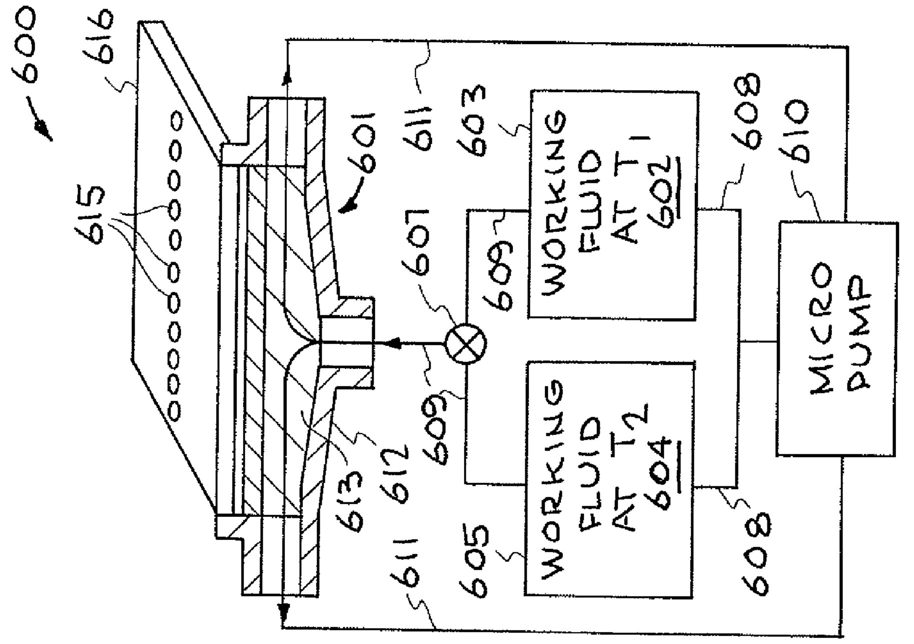
FIG. 6 illustrates an embodiment of the present invention wherein the material to be thermalcycled is contained on a microarray.

Referring now to FIG. 6, another embodiment of a thermal cycling system constructed in accordance with the present invention is illustrated. The system is designated generally by the reference numeral 600. The system 600 provides thermal cycling a material 615 to be thermal cycled between different temperatures using a microfluidic heat exchanger 601 operatively positioned with respect to the material 615 to be thermal cycled. The material 615 to be thermal cycled is contained on a microarray 116. Examples of microarrays are shown in U.S. Pat. No. 7,354,389 for a microarray detector and methods which states, "The present invention is directed to an analytic system for detection of a plurality of analytes that are bound to a biochip, wherein an optical detector uses registration markers illuminated by a first light source to determine a focal position for detection of the analytes that are illuminated by a second light source." U.S. Patent No. for a microarray detector and methods is incorporated herein by reference.

The system 600 includes the following additional structural components: microfluidic heat exchanger housing 612, porous medium 613, micropump 610, lines 611, chamber 603, working fluid 602 at $T_1$, chamber 605, working fluid 604 at $T_2$, lines 608, multi-position valve 607, and lines 609.

The structural components of the system 600 having been described, the operation of the system 600 will be explained. The multi-position valve 607 is actuated to provide flow of working fluid 602 at $T_1$ from chamber 603 to the microfluidic heat exchanger 601. Micro pump 610 is actuated driving working fluid 602 at $T_1$ from chamber 603 to the microfluidic heat exchanger 601. The working fluid 602 at $T_1$ passes through the porous medium 613 in the microfluidic heat exchanger 601 raising the temperature of the material to be thermal cycled 615 to temperature $T_1$. The porous medium 613 in the microfluidic heat exchanger 601 results in substantial surface area enhancement and increased fluid flow-path tortuosity, both of which enhance heat transfer and the resulting heat flux between the working fluid and the porous matrix.

Next the multi-position valve 607 is actuated to provide flow of working fluid 604 at $T_2$ from chamber 605 to the microfluidic heat exchanger 601. Micro pump 610 is actuated driving working fluid 604 at $T_2$ from chamber 605 to the microfluidic heat exchanger 601. The working fluid 602 at $T_2$ passes through the porous medium 613 in the microfluidic heat exchanger 601 lowering the temperature of the material to be thermal cycled 615 to temperature $T_2$.

The heat exchanger 601 of the system 600 utilizes inlet and exit channels where heating/cooling fluid 602 and 604 is passing through an enclosure, and microarray 616 containing the material to be thermal cycled. The heat exchange 601 is filled with a conductive porous medium 613 of uniform porosity and permeability. In another embodiment the enclosure is filled with a conductive porous medium 613 with a gradient porosity. The nominal permeability and porosity of the porous matrix are taken as $3.74\times10^{-10}$ $m^2$ and 0.45, respectively. The porous medium 613 is saturated with heating/cooling fluid 602, 604 coming through an inlet channel. The inlet channel will be connected to hot and cold supply tanks 603 and 605. The switching multi-position valve 607 is used to switch between hot 602 and cold tanks 605 for heating and cooling cycles. All lateral walls and top of the porous medium are insulated to minimize losses. The micropump 610 is positioned to drive the working fluids 602 and 605 directly into the microfluidic heat exchanger 601. By positioning the micropump 610 outside the hot and cold supply tanks 603 and 605 and lines to the microfluidic heat exchanger 601 it eliminates the time that would be required to bring the micropump 610 up to the new temperature after each change.

Results

Tests and analysis were performed that provided unexpected and superior results and performance of apparatus and methods of the present invention. Some of the results and analysis of apparatus and methods of the present invention are described in the article "rapid microfluidic thermal cycler for polymerase chain reaction nucleic acid amplification," by Shadi Mahjoob, Kambiz Vafai, and N. Reginald Beer in the *International Journal of Heat and Mass Transfer* 51 (2008) 2109-2122. The "Conclusions" section of the article states, "An innovative and comprehensive methodology for rapid thermal cycling utilizing porous inserts was presented for maintaining a uniform temperature within a PCR microchip consisting of all the pertinent layers. An optimized PCR design which is widely used in molecular biology is presented for accommodating rapid transient and steady cyclic thermal management applications. Compared to what is available in the literature, the presented PCR design has a considerably higher heating/cooling temperature ramps and lower required power while resulting in a very uniform temperature distribution at the substrate at each time step. A comprehensive investigation of various pertinent parameters on physical attributes of the PCR system was presented. All pertinent parameters were considered simultaneously leading to an optimized design." The article "rapid microfluidic thermal cycler for polymerase chain reaction nucleic acid amplification," by Shadi Mahjoob, Kambiz Vafai, and N. Reginald Beer in the *International Journal of Heat and Mass Transfer* 51 (2008) 2109-2122 is incorporated herein in it entirety by this reference.

Figure 7:
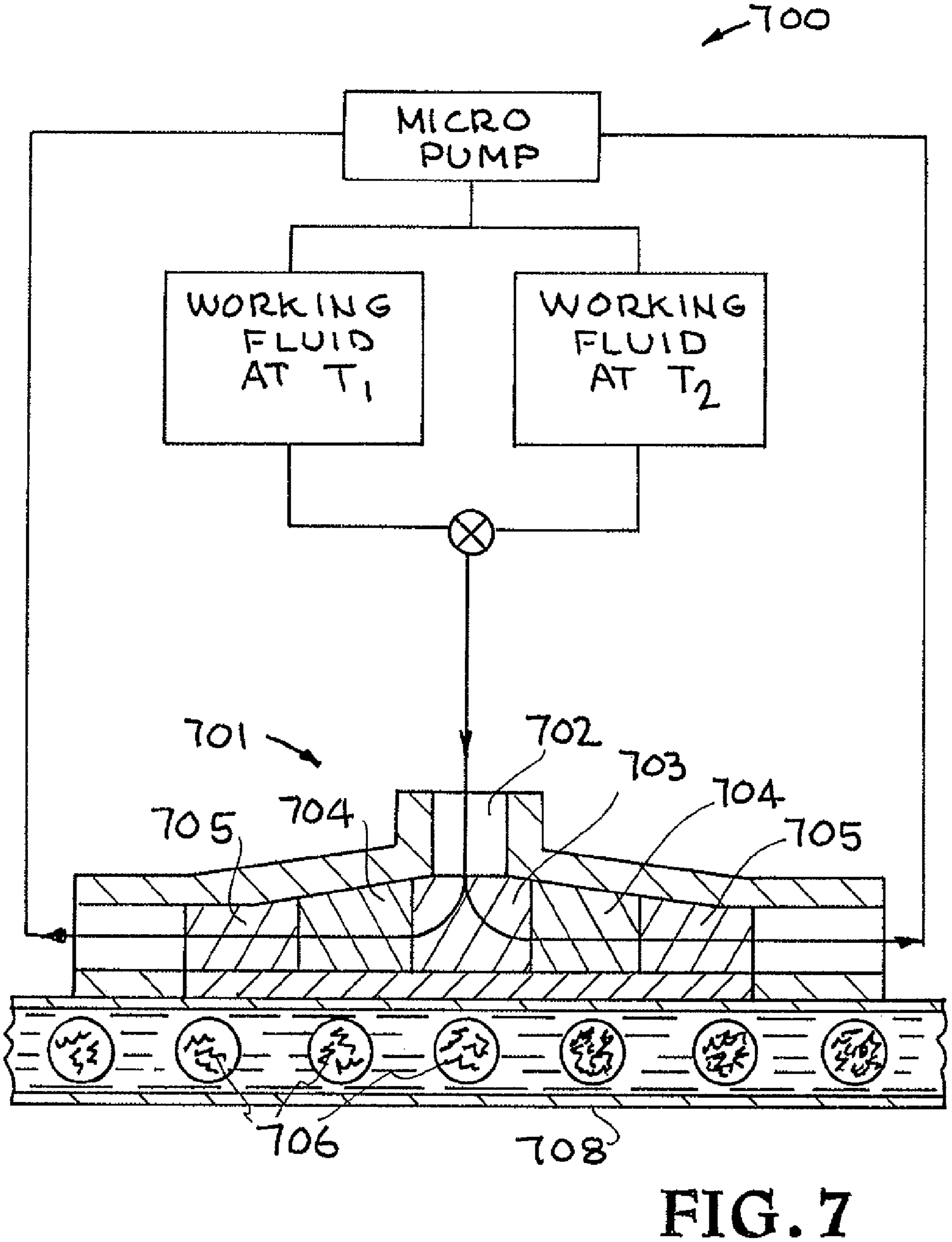
FIG. 7 illustrates another embodiment of the present invention.

Referring now to FIG. 7, another embodiment of a thermal cycling system constructed in accordance with the present invention is illustrated. The system is designated generally by the reference numeral 700. The system 700 provides thermal cycling of a material to be thermal cycled between a temperature $T_1$ and $T_2$ using a microfluidic heat exchanger 701 operatively positioned with respect to the material 706 to be thermal cycled. The material to be thermal cycled is positioned in contact with the microfluidic heat exchanger 701 as illustrated in the previous figures.

A working fluid at $T_1$ is provided and the working fluid at $T_1$ is flowed to the microfluidic heat exchanger 701 through the inlet 702. A working fluid at $T_2$ is provided and the working fluid at $T_2$ is flowed to the heat exchanger 701. The steps of flowing the working fluid at $T_1$ and at $T_2$ to the microfluidic heat exchanger 701 are repeated for a predetermined number of times. A porous medium is located in the microfluidic heat exchanger 701. The working fluids at $T_1$ and $T_2$ flow through the porous medium during the steps of flowing the working fluid at $T_1$ and $T_2$ through the microfluidic heat exchanger 701. The porous medium is a porous medium of gradient permeability and porosity. The porous medium is made up of a first porous medium 703, a second porous medium 704, and a third porous medium 705. The first porous medium 703, second porous medium 704, and third porous medium 705 have different permeability and porosity. The first porous medium 703, second porous medium 704, and third porous medium 705 are arrange to provide a gradient permeability and porosity.

The structural components of the system 700 having been described, the operation of the system 700 will be explained.

A valve is actuated to provide flow of working fluid at $T_1$ from a chamber to the microfluidic heat exchanger 701. A micro pump is actuated driving working fluid at $T_1$ from chamber to the microfluidic heat exchanger 701. The working fluid at $T_1$ passes through the porous medium in the microfluidic heat exchanger 701 raising the temperature of the material to be thermalcycled to temperature $T_1$. The porous medium with gradient permeability and porosity 703, 704, 705 in the microfluidic heat exchanger 701 results in microfluidic-scale elimination of laminar flow, inducing turbulence and thermal mixing and greatly enhancing heat transfer.

Next a valve is actuated to provide flow of working fluid at $T_2$ from a chamber to the microfluidic heat exchanger 701. A micro pump is actuated driving working fluid at $T_2$ from chamber to the microfluidic heat exchanger 701. The working fluid at $T_2$ passes through the porous medium 702 in the microfluidic heat exchanger 701 lowering the temperature of the material to be thermalcycled to temperature $T_2$. The steps of flowing the working fluid at $T_1$ and at $T_2$ to the microfluidic heat exchanger 701 are repeated for a predetermined number of times to provide the desired PCR. The porous medium with gradient permeability and porosity 703, 704, 705 in the microfluidic heat exchanger 701 results in substantial surface area enhancement and increased fluid flow-path tortuosity, both of which enhance heat transfer and the resulting heat flux between the working fluid and the porous matrix.

The aqueous channel 708 can be used to mix various assay components (i.e., analyte, oligonucleotides, primer, TaqMan probe, etc.) in preparation for amplification and detection. The channel geometry allows for dividing the sample into multiple aliquots for subsequent analysis serially or in parallel with multiple streams. Samples can be diluted in a continuous stream, partitioned into slugs, or emulsified into droplets. Furthermore, the nucleic acids may be in solution or hybridized to magnetic beads depending on the desired assay. The scalability of the architecture allows for multiple different reactions to be tested against aliquots from the same sample. Decontamination of the channels after a series of runs can easily be performed by flushing the channels with dilute solution of sodium hypochlorite, followed by deionized water.

The heat exchanger 701 of the system 700 utilizes inlet and exit channels where heating/cooling fluid is passing through, an enclosure, and a layer of conductive plate attached to a PCR micro-chip or microarray. The enclosure is filled with a conductive porous medium of gradient porosity and permeability. The porous medium is saturated with heating/cooling fluid coming through an inlet channel 702. The inlet channel will be connected to hot and cold supply tanks. A switching valve is used to switch between hot and cold tanks for heating and cooling cycles. All lateral walls and top of the porous medium are insulated to minimize losses.

Figure 8:
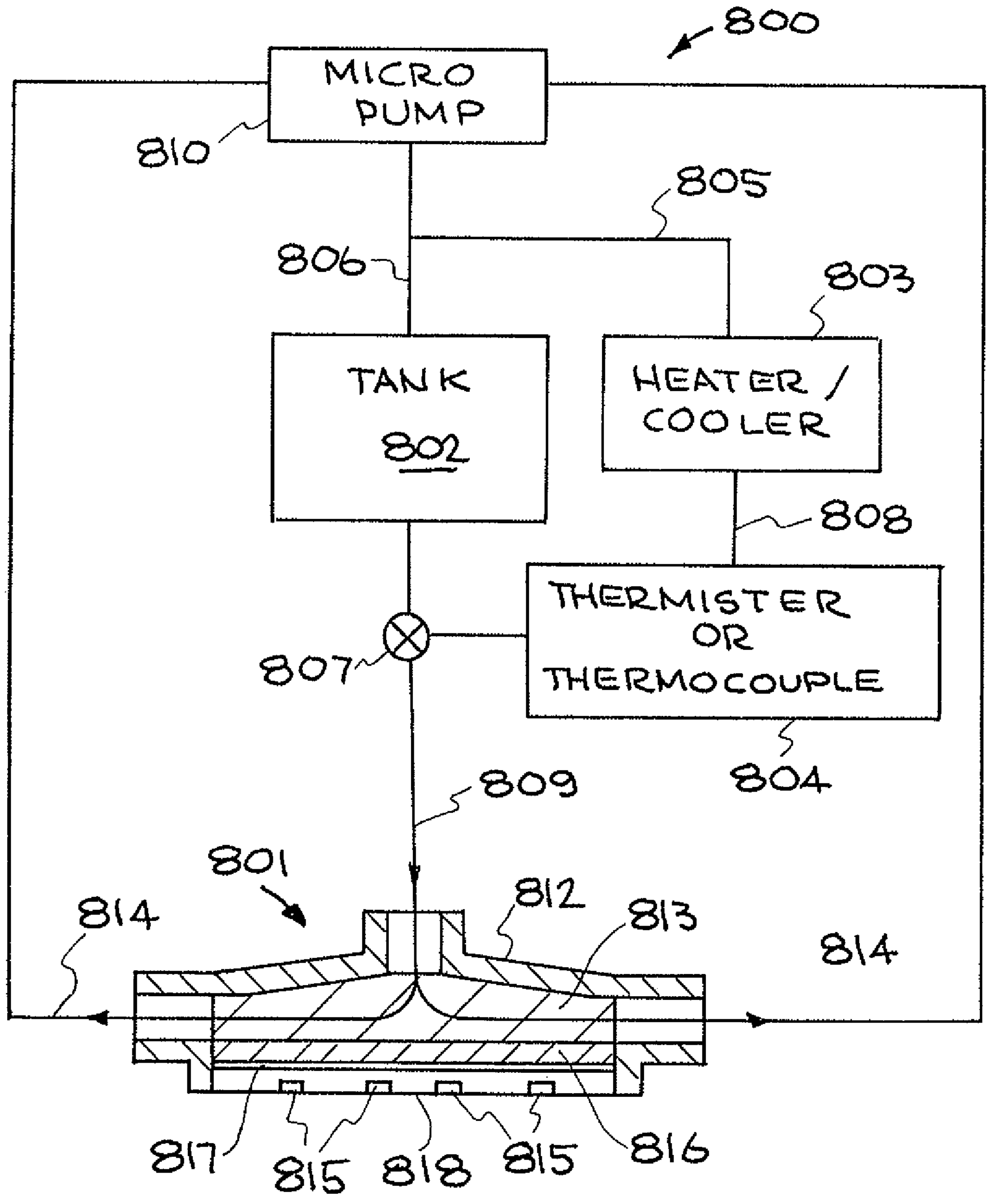
FIG. 8 illustrates yet another embodiment of the present invention.

Referring now to the drawings and in particular to FIG. 8, an embodiment of a system constructed in accordance with the present invention utilizing a single tank is illustrated. The system is designated generally by the reference numeral 800. The system 800 provides extremely fast continuous flow or batch PCR amplification of target nucleic acids in a compact, portable microfluidic-compatible platform. The system 800 provides a 1-tank version with a single tank 802 kept at a constant temperature and fed by a return line(s) 814 and 806 from the chip 818. The same return line(s) 814 and 806 feed both the tank 802 as well as a separate tank bypass line 805. The bypass line 805 is essentially a coil with or without heatsinks and fans blowing over it that connects to the variable valve just upstream of the chip input. By placing a thermister or thermocouple 804 upstream of the variable valve 807, it is possible to send working fluid at $T_1$ or $T_2$ or any temperature in-between, and only requires 1 tank and heating system.

The material 815 to be thermal cycled is contained on a chip 818 containing the DNA. The DNA sample 815 is contained on the chip 818 containing the DNA sample. A highly conductive plate 816 connects the chip 818 to the heat exchanger 801. Conductive grease 817 is used to provide thermal conductivity between the chip 818 and the heat exchanger 801. Instead of conductive grease 817 between the chip 818 and the heat exchanger 801 other forms of connection may be used. For example, press-fit contact or thermally-conductive tape may be used between the chip 818 and the heat exchanger 801.

The system 800 provides thermal cycling a material 815 (DNA Sample) to be thermal cycled between a temperature $T_1$ and $T_2$ or any temperature in between using a microfluidic heat exchanger 801 operatively positioned with respect to the material 815 to be thermal cycled. The steps of repeatedly flowing the working fluid at $T_1$ and at $T_2$ to the microfluidic heat exchanger 801 provide PCR fast and efficient nucleic acid analysis. The microfluidic polymerase chain reaction (PCR) thermal cycling method 800 is capable of extremely fast cycles, and a resulting extremely fast detection time for even long amplicons (amplified nucleic acids). The method 800 allows either singly or in combination: reagent and analyte mixing; cell, virion, or capsid lysing to release the target DNA if necessary; nucleic acid amplification through the polymerase chain reaction (PCR), and nucleic acid detection and characterization through optical or other means. An advantage of this system lies in its complete integration on a microfluidic platform and its extremely fast thermocycling.

The system 800 includes the following structural components: microfluidic heat exchanger 801, microfluidic heat exchanger housing 812, porous medium 813, micropump 810, lines 805, 806, 808, 809, and 814, multi position valve 807, highly conductive plate 816, thermal grease 817, chip containing DNA sample 818, and DNA sample 815.

The structural components of the system 800 having been described, the operation of the system 800 will be explained. The valve 807 is actuated to provide flow of working fluid at $T_1$ from tank 802 to the microfluidic heat exchanger 801. The system 800 provides a 1-tank version with you where the single tank 802 is kept at a constant temperature and is fed by a return line(s) 814 and 806 from the chip 818. The same return line(s) 814 and 806 however feeds both the tank 802 as well as a separate tank bypass line 805. The bypass line 805 is essentially a coil with or without heatsinks and fans blowing over it that connects to the variable valve just upstream of the chip input. By placing a thermister or thermocouple 804 upstream of the variable valve 807, it is possible to send working fluid at $T_1$ or $T_2$ or any temperature in-between, and only requires 1 tank and heating system.

The porous medium 813 in the microfluidic heat exchanger 801 results in substantial surface area enhancement and increased fluid flow-path tortuosity, both of which enhance heat transfer and the resulting heat flux between the working fluid and the porous matrix. The heat exchanger 801 of the system 800 utilizes inlet and exit channels where heating/cooling fluid is passing through, an enclosure, and a layer of conductive plate attached to a PCR micro-chip. The enclosure is filled with a conductive porous medium 813 of uniform or gradient porosity and permeability. The porous medium 813 is saturated with heating/cooling fluid coming through an inlet channel. The switching valve 807 is used to switch between hot and cold for heating and cooling cycles. All lateral walls and top of the porous medium are insulated to minimize losses. The micropump 810 is positioned to drive the working fluids directly into the microfluidic heat exchanger 801. By positioning the micropump 810 outside the hot and cold supply tanks it eliminates the time that would be required to bring the micropump 810 up to the new temperature after each change.

The systems described above can include reprogrammable intermediate steps. The reprogrammable intermediate steps are described as follows and can be used with the systems described in connection with FIGS. 1-8:

A) With 2 tanks and the variable electronically-controlled valve, a thermal sensor upstream of the valve that is running under automated closed loop control provides the ability to adjust the ratios of the volume of flow from the $T_1$ and $T_2$ reservoirs. By adjusting these ratios ANY temperature between (and including) $T_1$ and $T_2$ are attainable. So say a thermal setpoint for $T_3$ is known by the user, they input $T_1$, $T_2$, & $T_3$ into their keypad, PC, pendant, etc and the machine can thermal cycle between $T_1$ and $T_2$ and stop at $T_3$ if desired. For that matter, there can be multiple different "$T_3$'s" as long as they are between $T_1$ and $T_2$.

B) This capability would be highly desirable for PCR since most protocols are 3-step, that is they cycle from the annealing (low) temperature (~50 C) to an extension temperature (~70 C) which is the temperature that the DNA polymerase enzyme performs optimally, to the high temperature (~94 C) where the doubles strands separate. The sample is then brought back down to the anneal temp (~50 C) and the cycle repeats. An example of the complete thermal cycling protocol, including one time reverse transcription (converts RNA to DNA) and enzyme activation ("hot start") is given in the Experimental section (page 1855) of the publication "On-Chip Single-Copy Real-Time Reverse-Transcription PCR in Isolated Picoliter Droplets," by N. Reginald Beer, Elizabeth K. Wheeler, Lorenna Lee-Houghton, Nicholas Watkins, Shanavaz Nasarabadi, Nicole Hebert, Patrick Leung, Don W. Arnold, Christopher G. Bailey, and Bill W. Colston in *Analytical Chemistry* Vol. 80, No. 6: Mar. 15, 2008 pages 1854-1858. The publication "On-Chip Single-Copy Real-Time Reverse-Transcription PCR in Isolated Picoliter Droplets," by N. Reginald Beer, Elizabeth K. Wheeler, Lorenna Lee-Houghton, Nicholas Watkins, Shanavaz Nasarabadi, Nicole Hebert, Patrick Leung, Don W. Arnold, Christopher G. Bailey, and Bill W. Colston in *Analytical Chemistry* Vol. 80, No. 6: Mar. 15, 2008 pages 1854-1858 is incorporated herein by reference.

C) This capability also provides the ability for powering small molecule amplification that has multiple temperature steps that repeat in cycles. As time goes on, more and more of these molecular amplifications (not necessarily using DNA) will enter the art.

D) This also may be useful in other general chemical or complex synthesis reactions where endothermal and exothermal steps are required, such that an array or multi-well plate attached to this thermal cycler receives new reagents pipetted in (robotically or manually) at different temperatures in the repeating cycle.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for thermal cycling a material, comprising:

a microfluidic heat exchanger comprising a porous medium, an inlet, and an outlet;

a microfluidic unit comprising an array of wells configured to receive the material to be thermal cycled, the microfluidic thermal cycling unit thermally coupled to the porous medium;

a first tank configured to contain a first fluid at a first temperature;

a second tank configured to contain a second fluid at a second temperature, a supply tank coupled to the microfluidic heat exchanger outlet, to the first tank, and to the second tank, the supply tank configured to receive fluid from the porous medium through the microfluidic heat exchanger outlet and to supply fluid to the first tank and the second tank;

a valve system coupled to the microfluidic heat exchanger inlet and configured to alternately couple the first tank and the second tank to the microfluidic heat exchanger inlet; and a pump configured to pump the first fluid from the first tank through the microfluidic heat exchanger inlet and into the porous medium in a first state, and to pump the second fluid from the second tank through the microfluidic heat exchanger inlet and into the porous medium in a second state, wherein fluid within the porous medium is pumped through the microfluidic outlet and into the supply tank when fluid is pumped into the porous medium through the microfluidic heat exchanger inlet.

2. The apparatus of claim 1, wherein the porous medium comprises a uniform porosity.

3. The apparatus of claim 1, wherein the porous medium comprises a gradient porosity.

4. The apparatus of claim 1, wherein the microfluidic unit comprises a chip comprising the array of wells containing the material to be thermal cycled.

5. The apparatus of claim 1, wherein the first fluid comprises a liquid fluid.

6. The apparatus of claim 1, wherein the first fluid comprises a gas fluid.

7. The apparatus of claim 1, wherein the first fluid comprises a liquid metal fluid.

8. The apparatus of claim 1, wherein the second fluid comprises a liquid fluid.

9. The apparatus of claim 1, wherein the second fluid comprises a gas fluid.

10. The apparatus of claim 1, wherein the second fluid comprises a liquid metal fluid.

11. An apparatus for thermal cycling a material, comprising:

a heat exchanger comprising a porous medium, an inlet, and an outlet;

a tray configured to receive the material to be thermal cycled, the tray thermally coupled to the porous medium;

a first tank configured to contain a first fluid a first temperature;

a second tank configured to contain a second fluid at a second temperature;

a third tank coupled to the heat exchanger outlet, the first tank, and the second tank, and configured to receive fluid from the porous medium through the heat exchanger output, to store a third fluid at a third temperature, and to provide the third fluid to the first tank and the second tank;

a valve system configured to alternately couple the first tank and the second tank to the heat exchanger inlet; and a pump configured pump fluid into the porous medium through the heat exchanger inlet, the pumped fluid comprising the first fluid when the valve system couples the first tank to the heat exchanger inlet and comprising the second fluid when the valve system couples the second tank to the heat exchanger inlet, the pump further configured to pump fluid from the porous medium into the third tank through the heat exchanger outlet.

12. The apparatus of claim 11, wherein the tray comprises a channel containing droplets containing the material to be thermal cycled.

13. The apparatus of claim 11, wherein the tray comprises a chip containing the material to be thermal cycled.

14. The apparatus of claim 11, wherein the porous medium comprises a uniform porosity.

15. The apparatus of claim 11, wherein the porous medium comprises a gradient porosity.

16. A method of thermal cycling a material using the apparatus of claim 1, comprising, for each of a plurality thermal cycles:

pumping the first fluid from the first tank into the porous medium through the microfluidic heat exchanger inlet for a first period of time, pumping the second fluid from the second tank into the porous medium through the microfluidic heat exchanger inlet for a second period of time.

17. A method of thermal cycling a material using the apparatus of claim 1, comprising, for each of a plurality of thermal cycles:

coupling, by the valve system, the first tank to the heat exchanger inlet;

pumping the first fluid into the porous medium for a first period of time;

coupling, by the valve system, the second tank to the heat exchanger inlet; and pumping the second fluid into the porous medium for a second period of time.

* * * * *